United States Patent
Kato (10) Patent No.: US 8,213,020 B2
(45) Date of Patent: Jul. 3, 2012

(54) OPTICAL TOMOGRAPHIC IMAGING APPARATUS INCLUDING A BEAM SCATTERING STRUCTURE

(75) Inventor: Kiichi Kato, Odawara (JP)

(73) Assignee: Fujifilm Corporation, Tokyo (JP)

( * ) Notice: Subject to any disclaimer, the term of this patent is extended or adjusted under 35 U.S.C. 154(b) by 451 days.

(21) Appl. No.: 12/498,126

(22) Filed: Jul. 6, 2009

(65) Prior Publication Data

US 2010/0002240 A1    Jan. 7, 2010

(30) Foreign Application Priority Data

Jul. 7, 2008    (JP) ................ 2008-177027

(51) Int. Cl.
*G01B 9/02*    (2006.01)
*A61B 1/06*    (2006.01)

(52) U.S. Cl. ........................ 356/497; 600/176
(58) Field of Classification Search ........... 356/479, 356/497; 600/425, 310, 101, 170, 176, 182

See application file for complete search history.

(56) References Cited

U.S. PATENT DOCUMENTS

| 4,649,151 | A | * | 3/1987 | Dougherty et al. | 514/410 |
| 5,976,175 | A | * | 11/1999 | Hirano et al. | 607/89 |
| 6,564,089 | B2 | | 5/2003 | Izatt et al. | |
| 6,615,072 | B1 | | 9/2003 | Izatt et al. | |
| 7,072,046 | B2 | | 7/2006 | Xie et al. | |
| 7,158,234 | B2 | | 1/2007 | Uchiyama et al. | |

FOREIGN PATENT DOCUMENTS

| JP | 2003-28791 A | 1/2003 |
| JP | 2004-223269 A | 8/2004 |

* cited by examiner

*Primary Examiner* — Hwa Lee
(74) *Attorney, Agent, or Firm* — Birch, Stewart, Kolasch & Birch, LLP (57) ABSTRACT

In the optical tomographic imaging apparatus according to an aspect of the present invention, since a stable light intensity can be secured for a reflected light beam of a measurement light beam reflected off of a transmitting surface of a probe outer casing as a returning light beam to an optical fiber, the optical path length difference between a reference light beam and the measurement light beam can be precisely adjusted by adjusting the optical path length of the reference light beam with an optical path length adjusting device. In addition, a signal of a measurement object can be reliably detected from a detection signal of an interference light beam detected by an interference light detecting device.

8 Claims, 9 Drawing Sheets

OPTICAL TOMOGRAPHIC IMAGING APPARATUS INCLUDING A BEAM SCATTERING STRUCTURE

BACKGROUND OF THE INVENTION

1. Field of the Invention

The present invention relates to an optical tomographic imaging apparatus and an optical probe, and in particular, to an optical tomographic imaging apparatus and an optical probe capable of stabilizing the light intensity of a returning light beam received by measurement optics such as an optical fiber which outputs a measurement light beam.

2. Description of the Related Art

Conventionally, there are known optical tomographic imaging apparatuses utilizing optical coherence tomography (OCT) measurement as a method of acquiring a tomographic image without dissecting a measurement object such as living tissue.

OCT measurement is an optical interferometric measurement method in which a light beam outputted from a light source is divided into two light beams, namely, a measurement light beam and a reference light beam, and which utilizes the fact that optical interference is only detected when respective optical path lengths of the measurement light beam and the reference light beam become consistent with each other within the range of a coherence length of the light source.

In addition, the measurement light beam is to be guided by an optical probe to a measurement object, and a returning light beam from the measurement object is to be also guided by the same optical probe. In such an optical probe, a transmitting surface capable of transmitting a measurement light beam or a returning light beam is formed on a portion of a probe outer casing of the optical probe. A light beam outputted from an optical fiber inside the optical probe passes through an optical system such as a lens or a prism and is then transmitted through the transmitting surface of the probe outer casing to be irradiated on the measurement object as a measurement light beam.

With respect to such an optical tomographic imaging apparatus, Japanese Patent Application Laid-Open No. 2003-028791 discloses a technique in which, for each different optical probe, optical path lengths of a reference light beam and a measurement light beam are adjusted so that the optical path lengths become approximately consistent with each other.

In addition, U.S. Pat. No. 7,158,234 discloses a technique for detecting a reflected light beam from an optical window that is a transmitting surface of a probe outer casing to adjust a focal point of a probe light beam and an optical path length difference between a reference light beam and a measurement light beam.

Furthermore, U.S. Pat. No. 6,564,089 and Japanese Patent Application Laid-Open No. 2004-223269 disclose techniques in which a light beam is obliquely outputted with respect to a transparent cover (sheath) covering an outermost surface of a catheter in order to reduce the intensity of a reflected light beam reflected off of the cover surface and to prevent multiple reflection ghosts from being generated in a measurement image.

SUMMARY OF THE INVENTION

A returning light beam that enters an optical fiber inside an optical probe includes, in addition to a reflected light beam of a measurement light beam transmitted through a transmitting surface (hereinafter referred to as a sheath surface) of a probe outer casing and reflected off of a measurement object, a reflected light beam of the measurement light beam reflected off of the sheath surface. The reflected light beam reflected off of the sheath surface is conceivably a regularly reflected light beam. A regularly reflected light beam is a reflected light beam whose output angle and incidence angle are equal to each other.

Figure 8A:
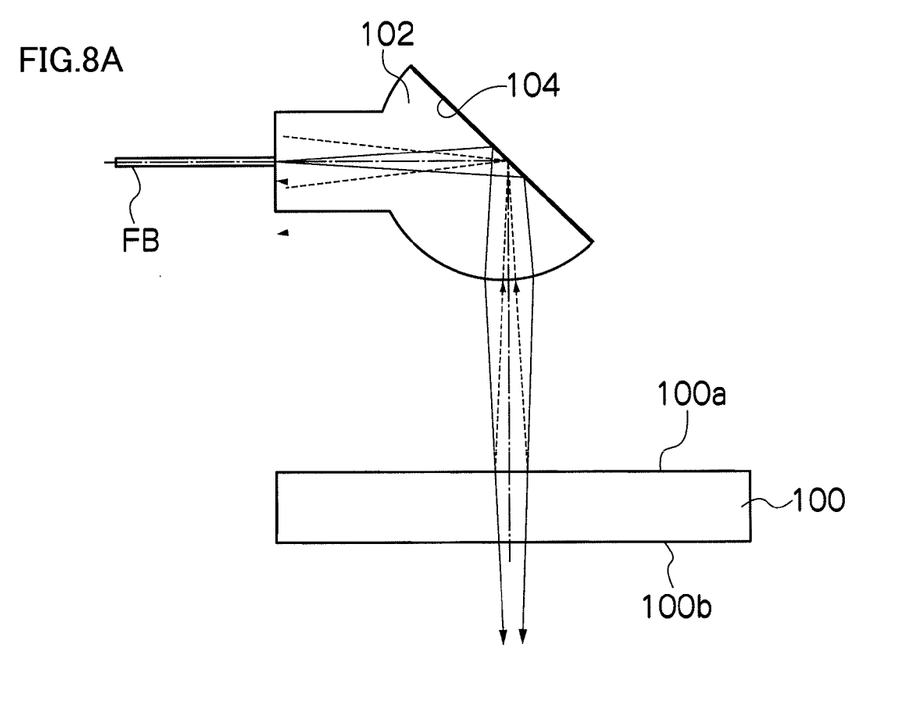
FIGS. 8A and 8B are diagrams showing an example of the behavior of a regularly reflected light beam at a sheath inner surface.
Figure 8B:
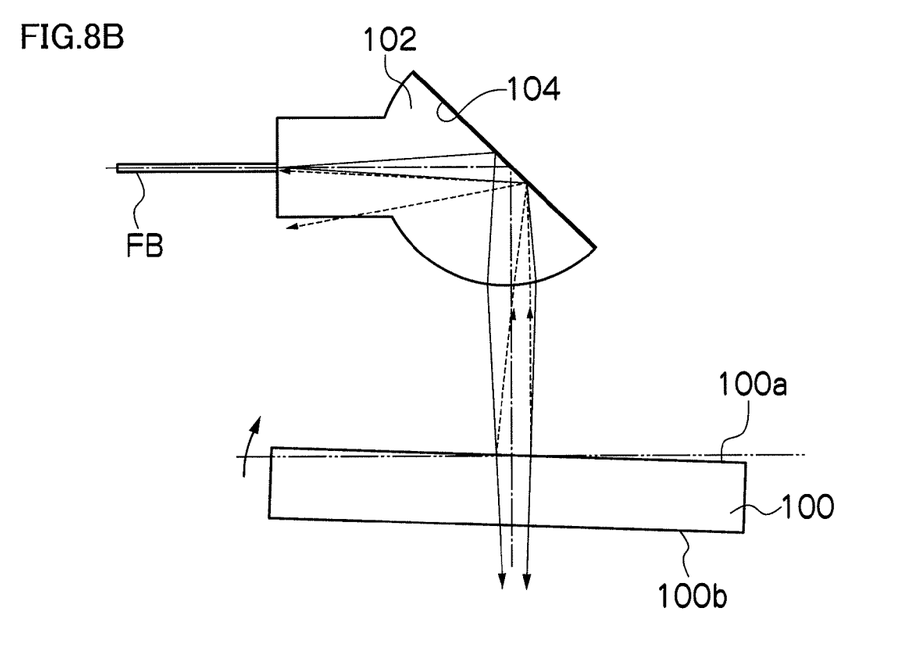

FIGS. 8A and 8B show an example of the behavior of a regularly reflected light beam reflected off of a sheath inner surface (the surface on the side of the interior of the optical probe among the sheath surfaces) in a case where the sheath surface is not relatively oblique to a reference plane and a case where the sheath surface is relatively oblique thereto. In this case, a reference plane refers to a plane that forms an approximately 90 degree angle with the optical axis of a measurement light beam outputted from an optical fiber FB and reflected and deflected by a reflecting surface 104 of an optical lens 102.

As shown in FIG. 8A, when a sheath inner surface 100a of a sheath 100 is not oblique to the reference plane, a regularly reflected light beam reflected off of the sheath inner surface 100a acquires a distribution spread at an end face of the optical fiber FB of which a portion enters the optical fiber FB.

However, as shown in FIG. 8B, when the sheath inner surface 100a is oblique to the reference plane (the plane depicted by the dashed-two dotted line in FIG. 8B), the regularly reflected light beam reflected off of the sheath inner surface 100a may deviate from the optical axis of the optical fiber FB, and may fail to enter the optical fiber FB. Therefore, a rapid decrease in the overall light intensity of the returning light beam to the optical fiber FB may occur.

The same description applies to a regularly reflected light beam reflected off of a sheath outer surface (the surface on the side of the exterior of the optical probe among the sheath surfaces).

The sheath inner surface 100a or the sheath outer surface 100b is likely to become oblique to the reference plane due to factors such as: a variation in the output angle attributable to the fabrication accuracy of measurement optics such as the optical fiber FB; the generation of an incline attributable to instability of the sheath inner surface 100a or the sheath outer surface 100b and of measurement optics; and angular variations of the sheath inner surface 100a or the sheath outer surface 100b attributable to bending of the optical probe. Therefore, the relative angle of the optical axis of a measurement light beam with respect to the sheath inner surface 100a or the sheath outer surface 100b is susceptible to variations and the variation range thereof is likely to become widened.

Consequently, due to variations in the relative angle of the optical axis of the measurement light beam with respect to the sheath inner surface 100a or the sheath outer surface 100b, having a regularly reflected light beam reflected off of the sheath inner surface 100a or the sheath outer surface 100b enter the optical fiber FB as a returning light beam causes the light intensity received by the optical fiber FB to vary significantly.

Moreover, when the light intensity received by the optical fiber FB varies significantly due to variations in the relative angle of the optical axis of the measurement light beam with respect to the sheath surface in this manner, for example, the technique described in Japanese Patent Application Laid-Open No. 2003-028791 may no longer be able to perform precise adjustment when approximately matching the optical path lengths of a reference light beam and a measurement light beam to each other. In addition, when the light intensity received by the optical fiber FB varies significantly in this manner, the technique described in U.S. Pat. No. 7,158,234 may no longer be capable of precisely adjusting a focal point of a probe light beam and an optical path length difference. Furthermore, the technique described in U.S. Pat. No. 6,564,089 and Japanese Patent Application Laid-Open No. 2004-223269 may no longer be able to control the light intensity of a returning light beam to an optical fiber.

The present invention has been made in consideration of such circumstances, and an object thereof is to provide an optical tomographic imaging apparatus capable of securing a stable light intensity with respect to a reflected light beam of a measurement light beam reflected off of a transmitting surface of a probe outer casing as a returning light beam to an optical fiber.

In order to achieve the object described above, an optical tomographic imaging apparatus according to a first aspect of the present invention comprises: an optical path length adjusting device which adjusts an optical path length of a reference light beam split from a source light beam outputted from a light source section; an optical probe having an optical fiber to which is entered a measurement light beam split from the source light beam, a lens that deflects and collects the measurement light beam outputted from the optical fiber, and a probe outer casing inside which the optical fiber and the lens are disposed and which is provided with a transmitting surface capable of transmitting the measurement light beam; and an interference light detecting device which detects an interference light beam from a multiplexed light beam produced by multiplexing the reference light beam whose optical path length has been adjusted by the optical path length adjusting device with a returning light beam from the optical probe, wherein an irregular corrugated structure is formed on the transmitting surface so that a part of a reflected light beam of the measurement light beam reflected off of the transmitting surface becomes scattered light beams.

According to the first aspect, since a stable light intensity can be secured for a reflected light beam of a measurement light beam reflected off of a transmitting surface of a probe outer casing as a returning light beam to an optical fiber, the optical path length difference between a reference light beam and the measurement light beam can be precisely adjusted by adjusting the optical path length of the reference light beam with an optical path length adjusting device.

In addition, a signal of a measurement object can be reliably detected from a detection signal of an interference light beam detected by an interference light detecting device.

An optical tomographic imaging apparatus according to a second aspect of the present invention is the optical tomographic imaging apparatus according to the first aspect thereof, wherein the irregular corrugated structure is an irregularly-pitched corrugated structure in which a minimum pitch of asperities of a corrugated structure is several times a wavelength of the measurement light beam.

According to the second aspect, a stable light intensity can be more reliably secured for a returning light beam to an optical fiber.

Here, a "minimum pitch of asperities" refers to a minimum value among distances between adjacent recesses or adjacent protrusions.

Moreover, for example, in order to provide scattering light beams with a spread of around 10 degrees with respect to a reflected light beam, setting the minimum pitch of asperities to about 5 to 6 times the wavelength of the measurement light beam shall suffice.

In order to achieve the object described above, an optical tomographic imaging apparatus according to a third aspect of the present invention is the optical tomographic imaging apparatus according to the first or the second aspect thereof, wherein a intensity of a reflected light beam of the measurement light beam reflected off of the transmitting surface and received by the optical fiber ranges between −90 dB and −50 dB, inclusive, with respect to a intensity of the measurement light beam outputted from the optical fiber.

According to the third aspect, a signal of a measurement object and a signal of a probe outer casing can be reliably detected from a detection signal of an interference light beam detected by an interference light detecting device.

In order to achieve the object described above, an optical tomographic imaging apparatus according to a fourth aspect of the present invention is the optical tomographic imaging apparatus according to any one of the first to third aspects thereof, wherein the irregular corrugated structure is a structure in which a depth of a asperities of a corrugated structure is equivalent to or less than ¼ a wavelength of the measurement light beam.

According to the fourth aspect, a major portion of a reflected light beam of a measurement light beam reflected off of a transmitting surface can be obtained as scattered light beams and, at the same time, sufficient irradiating light intensity to a measurement object can be obtained from a transmitted light beam of the measurement light beam at the transmitting surface.

In order to achieve the object described above, an optical tomographic imaging apparatus according to a fifth aspect of the present invention is the optical tomographic imaging apparatus according to any one of the first to fourth aspects thereof, wherein an incidence angle of a optical axis of the measurement light beam with respect to the transmitting surface is an angle such that a light intensity of a regularly reflected light beam is lower than a light intensity of the scattered light beams among the reflected light beam of the measurement light beam reflected off of the transmitting surface and received by the optical fiber.

According to the fifth aspect, a regularly reflected light beam included in a reflected light beam of a measurement light beam reflected off of a transmitting surface can be prevented from affecting a returning light beam to an optical fiber, and variations in the light intensity of the returning light beam to the optical fiber can be suppressed even when variations occur in the incidence angle of the optical axis of the measurement light beam with respect to the transmitting surface.

In order to achieve the object described above, an optical probe according to a sixth aspect of the present invention includes: a lens which deflects and collects an outgoing light beam outputted from an optical fiber; and a probe outer casing inside which the optical fiber and the lens are disposed and which is provided with a transmitting surface capable of transmitting the outgoing light beam; wherein an irregular corrugated structure is formed on the transmitting surface so that a part of a reflected light beam of the outgoing light beam reflected off of the transmitting surface becomes scattered light beams.

According to the sixth aspect, a stable light intensity can be secured for a reflected light beam of an outgoing light beam reflected off of a transmitting surface of a probe outer casing as a returning light beam to an optical fiber.

According to the present invention, a stable light intensity can be secured for a reflected light beam of a measurement light beam reflected off of a transmitting surface of a probe outer casing as a returning light beam to an optical fiber.

DETAILED DESCRIPTION OF THE PREFERRED EMBODIMENTS

An optical tomographic imaging apparatus and an optical probe according to the present invention will now be described in detail with reference to the attached drawings.
[Description of Optical Tomographic Imaging Apparatus]

Figure 1:
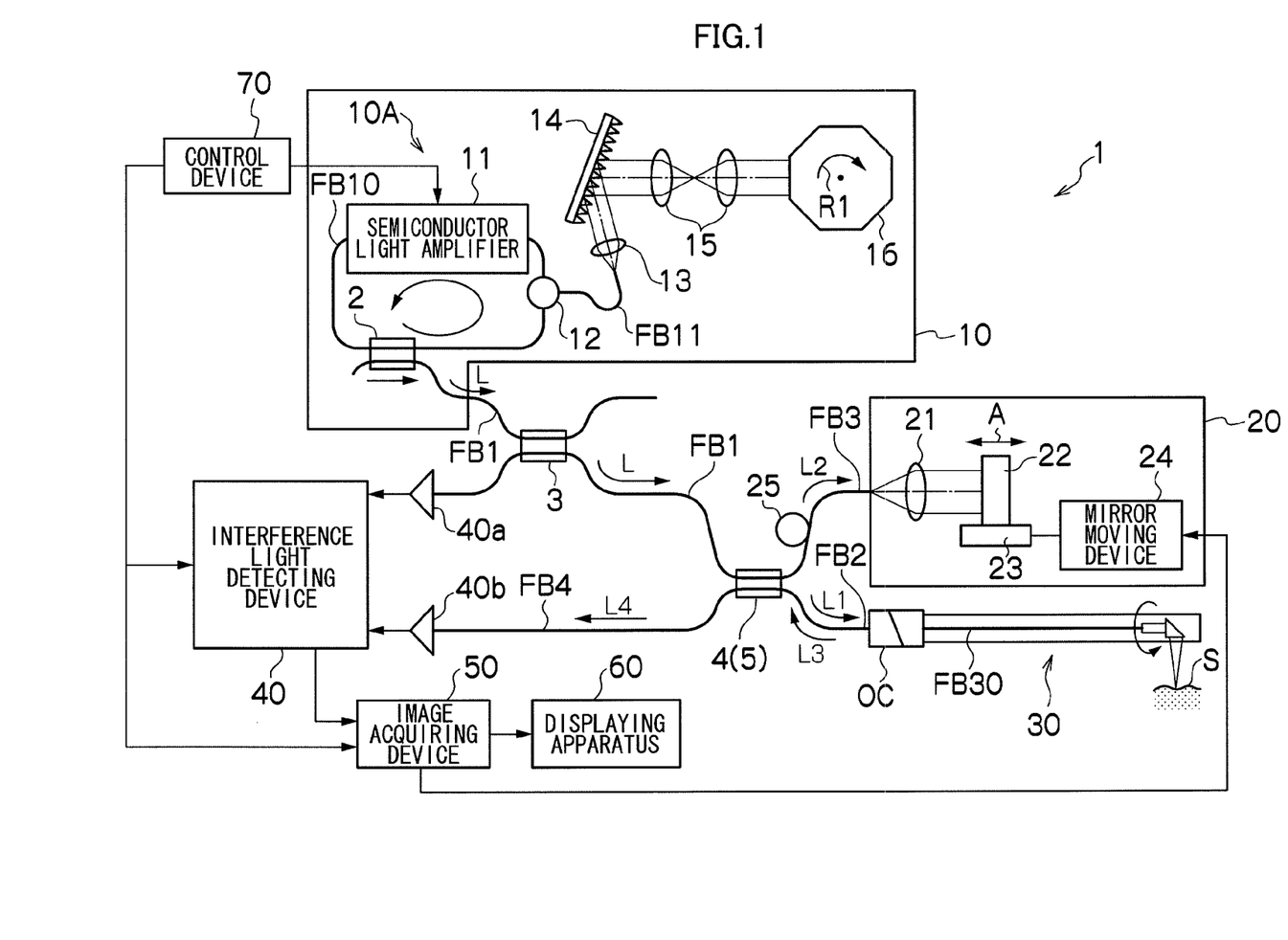
FIG. 1 is a block diagram showing a schematic configuration of an optical tomographic imaging apparatus.

FIG. 1 is a block diagram showing a schematic configuration of an optical tomographic imaging apparatus according to the present invention.

The optical tomographic imaging apparatus shown in FIG. 1 is an apparatus that acquires an optical tomographic image of a measurement object using optical coherence tomography (OCT) measurement.

The optical tomographic imaging apparatus 1 includes: a light source unit 10 that emits a laser light beam L; a light splitting device 4 which splits the laser light beam L emitted from the light source unit 10 into a measurement light beam L1 and a reference light beam L2; an optical path length adjusting device 20 that adjusts an optical path length of the reference light beam L2 split by the light splitting device 4; an optical probe 30 that guides the measurement light beam L1 split by the light splitting device 4 to a measurement object S; an optical multiplexing device 5 that multiplexes a returning light beam L3 from the measurement object S when the measurement light beam L1 is irradiated from the optical probe 30 onto the measurement object S with the reference light beam L2; an interference light detecting device 40 that detects an interference light beam L4 of the returning light beam L3 and the reference light beam L2 multiplexed by the optical multiplexing device 5; and an image acquiring device 50 that detects a reflection intensity of the measurement light beam at each depth position of the measurement object S and acquires a tomographic image of the measurement object S by analyzing the frequency of the interference light beam L4 detected by the interference light detecting device 40.

The light source unit 10 includes a laser light source 10A that emits a laser light beam L while sweeping frequencies at regular periods. The laser light source 10A includes: a semiconductor light amplifier (semiconductor gain medium) 11 and an optical fiber FB10. In addition, the laser light source 10A is structured such that the optical fiber FB10 is connected to both ends of the semiconductor light amplifier 11. The semiconductor light amplifier 11 functions to emit a weak emitted light beam to the side of one end of the optical fiber FB10 in response to the injection of a drive current, and to amplify a light beam that enters from the side of the other end of the optical fiber FB10. In addition, when the drive current is supplied to the semiconductor light amplifier 11, the laser light beam L is to be emitted to an optical fiber FB1 from an optical resonator formed by the semiconductor light amplifier 11 and the optical fiber FB10.

Furthermore, an optical bifurcator 12 is coupled to the optical fiber FB10, whereby a part of a light beam guided through the optical fiber FB10 is arranged so as to be emitted from the optical bifurcator 12 to the side of an optical fiber FB11. A light beam emitted from the optical fiber FB11 is reflected by a rotary polygon mirror (polygon mirror) 16 via a collimator lens 13, a diffraction grating element 14, and an optical system 15. The reflected light beam reenters the optical fiber FB11 via the optical system 15, the diffraction grating element 14, and the collimator lens 13.

In this case, the rotary polygon mirror 16 rotates in the direction of arrow R1, and is arranged so that the angle of each reflecting surface changes with respect to the optical axis of the optical system 15. Accordingly, only a light beam of a specific frequency range among light beams separated at the diffraction grating element 14 returns to the optical fiber FB11. The frequency of the light beam that returns to the optical fiber FB11 is determined by an angle formed by the optical axis of the optical system 15 and a reflecting surface. A light beam of a specific frequency range having entered the optical fiber FB11 enters the optical fiber FB10 from the optical bifurcator 12 and, as a result, a laser light beam L of a specific frequency range is emitted to the side of the optical fiber FB11. Therefore, when the rotary polygon mirror 16 rotates at a constant speed in the direction of arrow R1, the wavelength of a light beam reentering the optical fiber FB11 is to be swept at regular periods. In other words, a laser light beam L whose wavelength is swept at regular periods is emitted from the light source unit 10 to the side of the optical fiber FB1.

The light splitting device 4 shown in FIG. 1 is made up of, for example, 2×2 optical fiber couplers, and is arranged so as to split a laser light beam L guided from the light source unit 10 via the optical fiber FB1 into the measurement light beam L1 and the reference light beam L2. The light splitting device 4 is optically connected to two optical fibers FB2 and FB3 respectively, whereby the measurement light beam L1 is to be guided to the side of the optical fiber FB2 while the reference light beam L2 is to be guided to the side of the optical fiber FB3. In FIG. 1, the light splitting device 4 also functions as an optical multiplexing device 5.

The optical probe 30 is optically connected to the optical fiber FB2, whereby the measurement light beam L1 is to be guided from the optical fiber FB2 to the optical probe 30. The optical probe 30 is arranged so as to be, for example, inserted into a body cavity via a forceps channel from a forceps opening, and is removably mounted to the optical fiber FB2 by an optical connector OC.

Meanwhile, the optical path length adjusting device 20 is disposed on the emitting side of the reference light beam L2 of the optical fiber FB3. The optical path length adjusting device 20 is arranged so as to change the optical path length of the reference light beam L2 in order to adjust the position where the measurement of the measurement object S is to be commenced, and includes a collimator lens 21 and a reflecting mirror 22. The reference light beam L2 emitted from the optical fiber FB3 is transmitted through the collimator lens 21 and then reflected by the reflecting mirror 22, and is once again transmitted through the collimator lens 21 before entering the optical fiber FB3.

The reflecting mirror 22 is disposed on a movable stage 23. The movable stage 23 is provided so as to be movable in the direction of arrow A by a mirror moving device 24. The optical path length of the reference light beam L2 changes in correspondence with the movement of the movable stage 23 in the direction of arrow A.

The optical multiplexing device 5 is made up of 2×2 optical fiber couplers and is arranged so as to multiplex the reference light beam L2 whose frequency has been shifted and optical path length has been changed by the optical path length adjusting device 20 with the returning light beam L3 from the measurement object S, and to emit the same to the side of the interference light detecting device 40 via an optical fiber FB4.

The interference light detecting device 40 is arranged so as to detect the interference light beam L4 of the returning light beam L3 and the reference light beam L2 multiplexed by the optical multiplexing device 5, and is made up of, for example, a photodiode. The image acquiring device 50 acquires a tomographic image of the measurement object S by performing frequency analysis on a signal of the interference light beam L4 detected by the interference light detecting device 40. The tomographic image acquired by the image acquiring device 50 is arranged so as to be displayed on a displaying apparatus 60.

Moreover, the embodiment shown in FIG. 1 is provided with a detector 40a that detects a light intensity of a laser light beam L bifurcated from an optical fiber coupler 3 of the optical fiber FB1 and a detector 40b that detects a light intensity of the interference light beam L4. The interference light detecting device 40 functions to adjust the balance of the light intensity of the interference light beam L4 based on an output from the detector 40a. Due to this function, the influence of light intensity variations in each frequency can be suppressed and a clearer image can be obtained. In addition, the interference light detecting device 40 is equipped with a spectral sensitivity characteristic enabling detection of a light beam with a wavelength band of the laser light beam L.

Furthermore, a control device 70 controls the semiconductor light amplifier 11, the interference light detecting device 40, and the image acquiring device 50.

An example of operations of the optical tomographic imaging apparatus 1 will now be described. First, as a result of a movement of the movable stage 23 in the direction of arrow A, optical path length adjustment is performed so that the measurement object S is positioned within a measurable range. Subsequently, a laser light beam L whose wavelength has been swept at regular periods is emitted from the light source unit 10, whereby the laser light beam L is split into the measurement light beam L1 and the reference light beam L2 by the light splitting device 4. The measurement light beam L1 is guided into a body cavity by the optical probe 30 and irradiated on the measurement object S. Then, the returning light beam L3 from the measurement object S is multiplexed with the reference light beam L2 reflected off of the reflecting mirror 22, and the interference light beam L4 of the returning light beam L3 and the reference light beam L2 is detected by the interference light detecting device 40. The image acquiring device 50 performs frequency analysis on a signal of the detected interference light beam L4 to acquire a tomographic image. As shown, the optical tomographic imaging apparatus 1 that acquires a tomographic image using SS-OCT measurement is arranged to acquire image information at each depth position based on the frequency and the light intensity of the interference light beam L4. The movement of the reflecting mirror 22 in the direction of arrow A is used for adjusting the position at which measurement is to be commenced.

[Description of Optical Probe]

Next, the optical probe 30 will be described.

Figure 2:
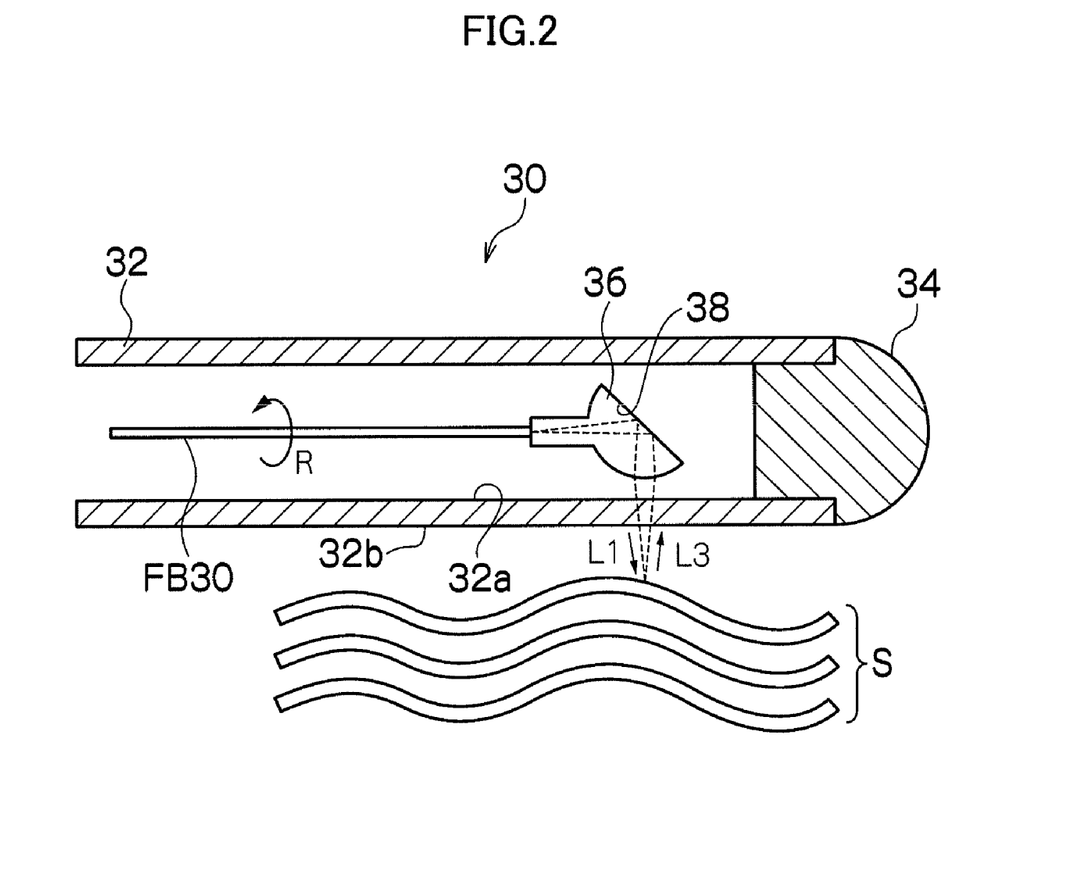
FIG. 2 is a partial cross-sectional diagram showing an enlargement of a tip of an optical probe.

FIG. 2 is a partial cross-sectional diagram showing an enlargement of a tip of the optical probe 30.

As shown in FIG. 2, the optical probe 30 according to the present embodiment includes: a sheath 32; a cap 34; an optical fiber FB30; an optical lens 36 having a total reflecting surface 38 with an angle of approximately 45 degrees, and the like.

The sheath 32 is a flexible and tubular probe outer casing made up of a material that transmits the measurement light beam L1 and the returning light beam L3, and is arranged so that an entire surface thereof is transmissive. Moreover, the sheath 32 may have a transmitting surface whose entire circumference is formed of a light transmissive material (transparent material) on at least a portion on the side of a tip (a tip of the sheath 32 opposite to the optical connector OC, hereinafter referred to as a tip of the sheath 32) through which the measurement light beam L1 and the returning light beam L3 are transmitted.

Among the transmitting surfaces of the sheath 32, an inner surface shall be referred to as a sheath inner surface 32a and an outer surface as a sheath outer surface 32b.

A cap 34 is provided at the tip of the sheath 32 and blocks the tip of the sheath 32.

The optical fiber FB30 is a linear member housed in the sheath 32 along the same. The measurement light beam L1 emitted from the optical fiber FB2 enters the optical fiber FB30, whereby the optical fiber FB30 guides the measurement light beam L1 to the optical lens 36. In addition, the optical fiber FB30 guides the returning light beam L3 from the measurement object S acquired by the optical lens 36 when the measurement light beam L1 is irradiated on the measurement object S to the optical connector OC, and causes the returning light beam L3 to enter the optical fiber FB2.

In this case, the optical fiber FB30 and the optical fiber FB2 are connected by the optical connector OC. The optical fiber FB30 and the optical fiber FB2 are optically connected in a state where the rotation of the optical fiber FB30 is not transmitted to the optical fiber FB2. Furthermore, the optical fiber FB30 is disposed in a rotatable state with respect to the sheath 32.

The optical lens 36 is disposed at a measurement-side tip (the tip of the optical fiber FB30 opposite to the optical connector OC). A tip of the optical lens 36 is formed in an approximately spherical shape such that the optical lens 36 deflects the measurement light beam L1 emitted from the optical fiber FB30 and collects the same on the measurement object S.

The optical lens 36 causes the measurement light beam L1 emitted from the optical fiber FB30 to be deflected by the total reflecting surface 38 and irradiated onto the measurement object S, and causes the returning light beam L3 from the measurement object S to be collected and entered into the optical fiber FB30.

In addition, the optical fiber FB30 is rotatable by the optical connector OC. By rotating the optical fiber FB30, the optical lens 36 is rotated in the direction of arrow R with respect to the sheath 32. Furthermore, the optical connector OC includes a rotation encoder and detects an irradiating position of the measurement light beam L1 from positional information (angular information) of the optical lens 36 based on a signal from the rotation encoder. In other words, a measurement position is detected by detecting an angle of the rotating optical lens 36 in the rotational direction with respect to a reference position.

When the optical connector OC rotates the optical fiber FB30 in the direction of arrow R shown in FIG. 2, the optical probe 30 irradiates the measurement light beam L1 emitted from the optical lens 36 onto the measurement object S while scanning in the direction of arrow R (a circumferential direction of the sheath 32), and acquires the returning light beam L3.

Accordingly, a desired site of the measurement object S can be accurately targeted and a returning light beam L3 reflected off of the measurement object S can be acquired across the entire periphery in the circumferential direction of the sheath 32.

[Description of Light Intensity Stabilization of Returning Light Beam]

The present invention proposes a method employed by the optical probe 30 configured as described above of stabilizing a light intensity of a returning light beam to the optical fiber FB30.

Since a measurable range of the optical tomographic imaging apparatus 1 is in the order of several millimeters when it is assumed that a position where the optical path lengths of the measurement light beam L1 and the reference light beam L2 are equal to each other is an origin thereof, the optical path length difference between the measurement light beam L1 and the reference light beam L2 must be accurately adjusted so that the measurement object S reliably falls within the measurable range. The adjustment of the optical path length difference between the measurement light beam L1 and the reference light beam L2 is performed by adjusting the optical path length adjusting device 20 of a retarding optics based on an OCT signal that is an interference signal detected by the interference light detecting device 40.

FIGS. 3A, 3B, 3C, and 3D are diagrams showing the behavior of OCT signals. In the drawing, the abscissas represent relative distance within the measurable range and the ordinates represent signal values of an OCT signal.

Figure 3A:
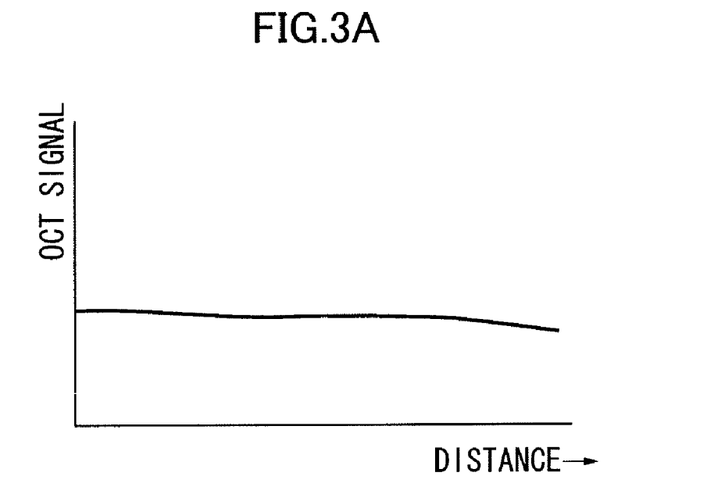
FIGS. 3A, 3B, 3C, and 3D are diagrams showing the behavior of OCT signals.
Figure 3B:
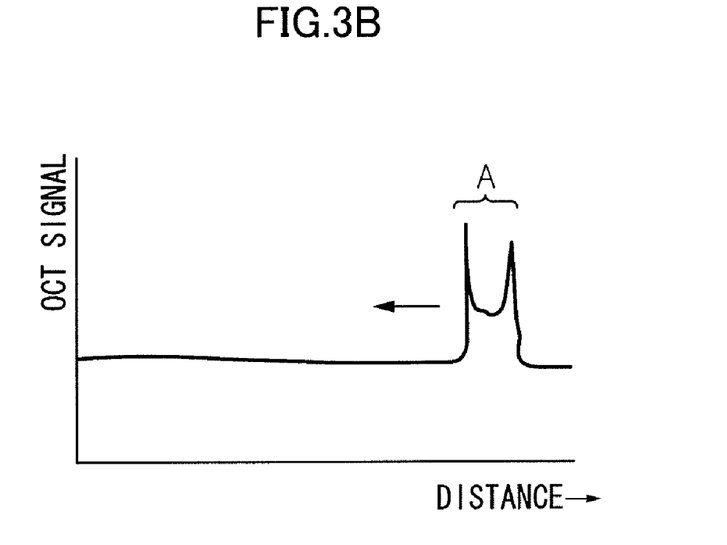
Figure 3C:
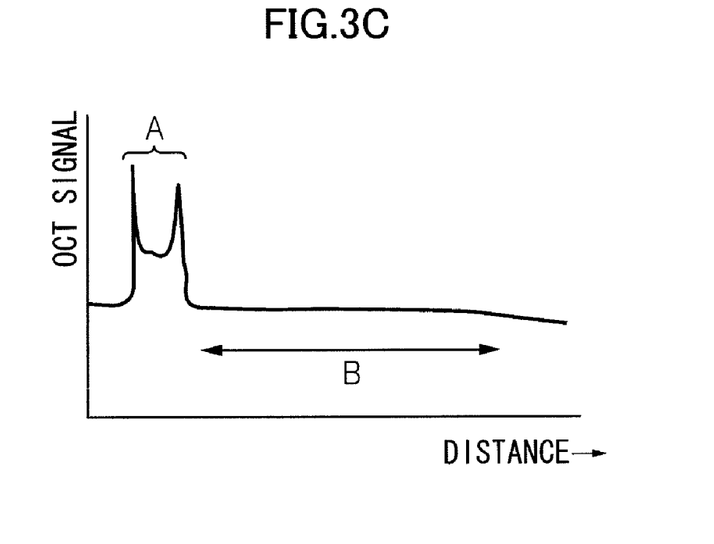
Figure 3D:
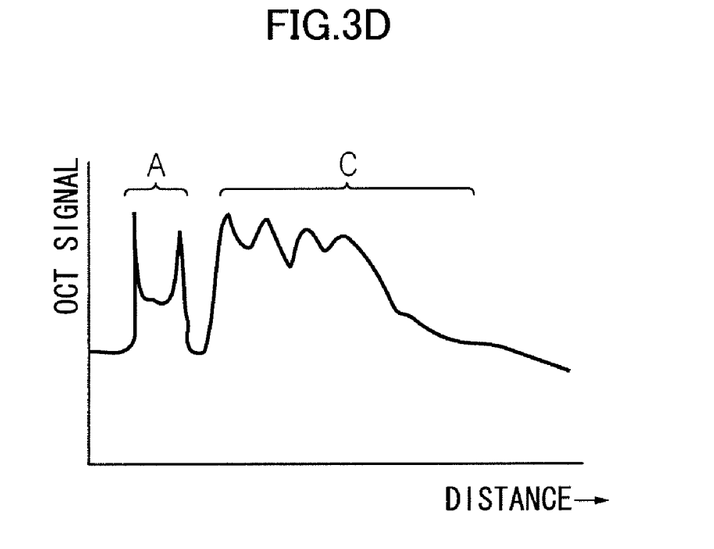

FIG. 3A shows an OCT signal in a state where the sheath 32 is outside of the measurable range; FIG. 3B shows an OCT signal in a state where the optical path length adjusting device 20 has been adjusted and the sheath 32 has entered the measurable range; FIG. 3C shows an OCT signal in a state where the optical path length adjusting device 20 has been further fine-adjusted and the measurement object S has entered the measurable range; and FIG. 3D shows an OCT signal in a state where measurement has actually been performed on the measurement object S.

As shown in FIG. 3A, in a state where the sheath 32 is outside of the measurable range, the OCT signal remains under a certain value.

However, as shown in FIG. 3B, when the optical path length adjusting device 20 is adjusted to create a state where the sheath 32 has entered the measurable range, the OCT signal takes a high value at a measurement position corresponding to the sheath 32 due to the influence of the reflected light beam of the measurement light beam reflected off of the sheath 32 (the region designated by reference character A in the drawing). In particular, high values of the OCT signal appear at regular intervals in portions corresponding to the sheath inner surface 32a and the sheath outer surface 32b, and a detection signal of the sheath 32 which is characteristic and readily identifiable is detected on the OCT signal.

In OCT measurement, when the measurement object S is a living body, measurement is often performed by bringing the sheath outer surface 32b into close contact with the living body. Therefore, it is desirable to set an optimal measurement range that is a measurement range optimal for measuring the measurement object S to the vicinity of the sheath outer surface 32b.

To this end, referring to a detection signal of the sheath 32 (the signal designated by reference character A in the drawing) such as shown in FIG. 3B, the optical path length adjusting device 20 is further adjusted so that, as shown in FIG. 3C, an optimal measurement range (the range designated by reference character B in the drawing) is set to be positioned in the vicinity of the detection signal of the sheath 32 within the measurable range or, more specifically, in the vicinity of the detection signal of the sheath outer surface 32b.

When a measurement of the measurement object S is actually started by setting the measurable range as described above, as shown in FIG. 3D, a detection signal of the measurement object S (the signal designated by reference character C in the drawing) is detected in the optimal measurement range from the OCT signal.

In this case, the value of the detection signal of the sheath 32 varies according to the light intensity of the reflected light beam of the measurement light beam reflected off of the sheath 32 entering the optical fiber FB30.

When the value of the detection signal of the sheath 32 is extremely small, the detection signal of the sheath 32 cannot be clearly recognized from the OCT signal, thereby making it difficult to accurately set the aforementioned optimal measurement range by adjusting the optical path length adjusting device 20.

As a specific example of an OCT signal detection sensitivity, for a detection signal to be detected in an OCT signal, it is necessary that the intensity of a returning light beam received by the optical fiber FB30 with respect to the intensity of the measurement light beam L1 outputted from the optical fiber FB30 (hereinafter referred to as a returning light intensity) be at least in the order of −100 dB. In addition, for a detection signal of the sheath 32 to be clearly recognized in an OCT signal, an intensity difference of at least 10 to 20 dB with respect to the detection intensity of the OCT signal is required.

On the other hand, when the value of a detection signal of the sheath 32 is significantly greater than the value of a detection signal of the measurement object S, the dynamic range of a signal processing system is consumed, adversely affecting signal detection such as making low-level signals among the detection signals of the measurement object S undetectable.

In consideration thereof, assuming that the returning light intensity of a light beam returning from the vicinity of the surface of the measurement object S is −50 dB or lower, then the light intensity of a returning light beam from the sheath 32 must be stabilized at −90 to −50 dB.

Figure 4:
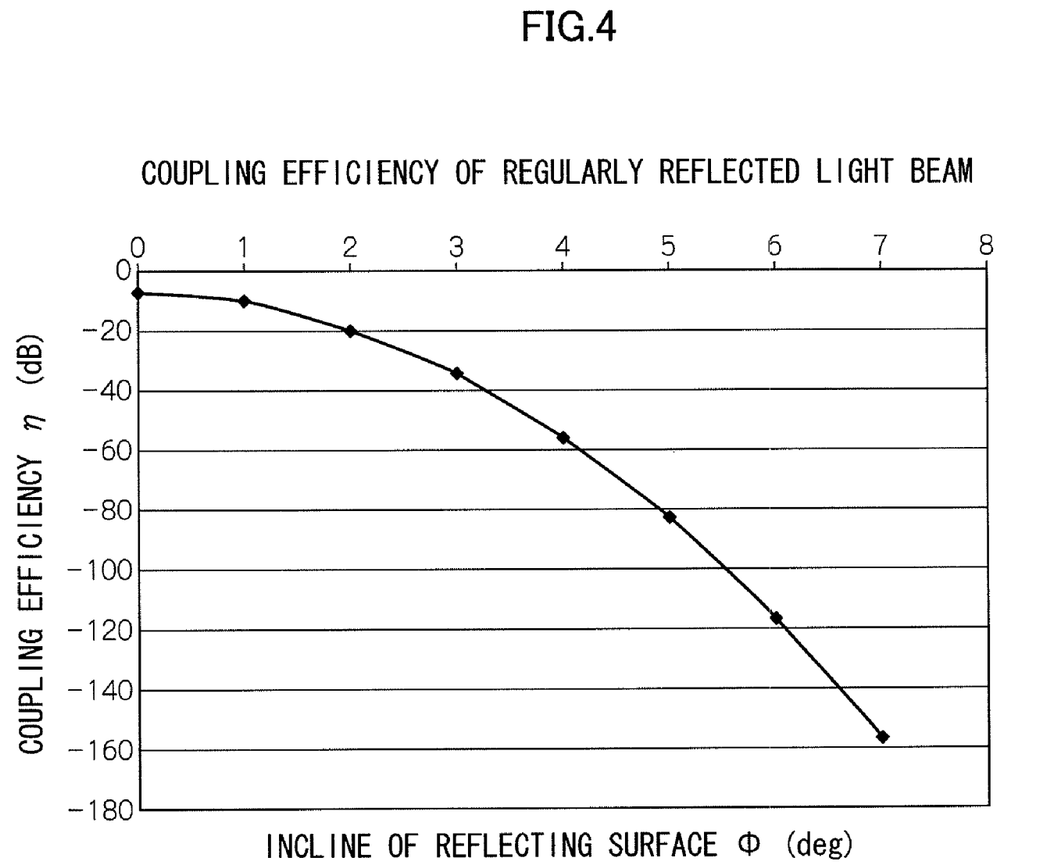
FIG. 4 is a diagram showing a calculated coupling efficiency η of a reflected light beam of a measurement light beam reflected off of a sheath in a case where the reflected light beam is a regularly reflected light beam.

FIG. 4 is a diagram showing a calculated coupling efficiency η of a reflected light beam of the measurement light beam L1 reflected off of the sheath 32 in a case where the reflected light beam is a regularly reflected light beam. Here, the coupling efficiency η represents the proportion of the light intensity of an incoming light beam with respect to the light intensity of an outgoing light beam at an end face of the optical fiber FB30, and corresponds to the returning light intensity described earlier.

In FIG. 4, the sheath inner surface 32a when the optical axis of the measurement light beam L1 forms an incidence angle of 90 degrees with respect to the sheath 32 is assumed to be the reference plane, and a relative incline of the sheath inner surface 32a is calculated as reference character φ. As shown in FIG. 4, the coupling efficiency η of the reflected light beam decreases rapidly as the incline φ increases. Specifically, while the coupling efficiency η is around −10 dB when the incline φ is within the range of 0 to 1 degrees, the coupling efficiency η rapidly decreases to around −100 dB when the incline φ ranges within 5 to 6 degrees.

Therefore, as described earlier, if it is assumed that a returning light intensity of around −100 dB is required for a detection signal to be detected in an OCT signal, when the reflected light beam of the measurement light beam L1 reflected off of the sheath 32 is a regularly reflected light beam, the returning light intensity may fail to reach an OCT signal detection sensitivity at an incline φ ranging within 5 to 6 degrees, thereby presenting a risk that a detection signal of the sheath 32 may not be clearly recognized from an OCT signal.

In consideration thereof, the present invention proposes to stabilize the light intensity of a returning light beam entering the optical fiber FB30 and stabilize the value of a detection signal of the sheath 32 in an OCT signal by arranging at least a portion of a reflected light beam of at least one of the sheath inner surface 32a and the sheath outer surface 32b to be scattered light beams.

Specifically, a fine corrugated structure is formed on either one of the sheath inner surface 32a and the sheath outer surface 32b or on both the sheath inner surface 32a and the sheath outer surface 32b.

Figure 5A:
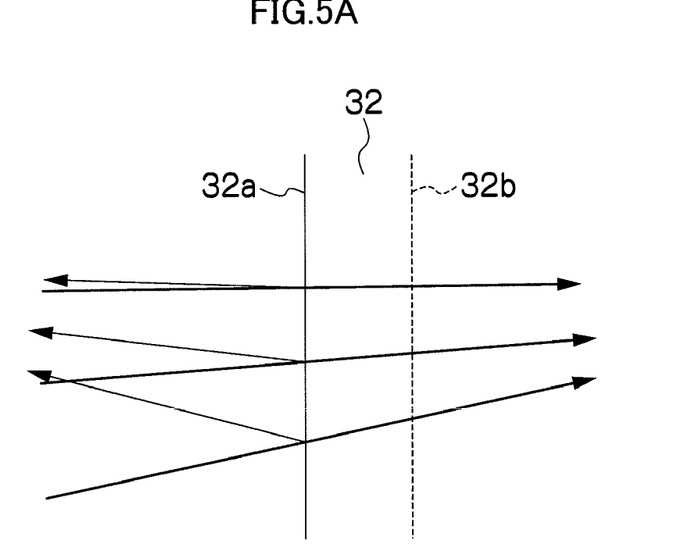
FIGS. 5A and 5B are diagrams showing reflected light beams and transmitted light beams at a sheath inner surface.
Figure 5B:
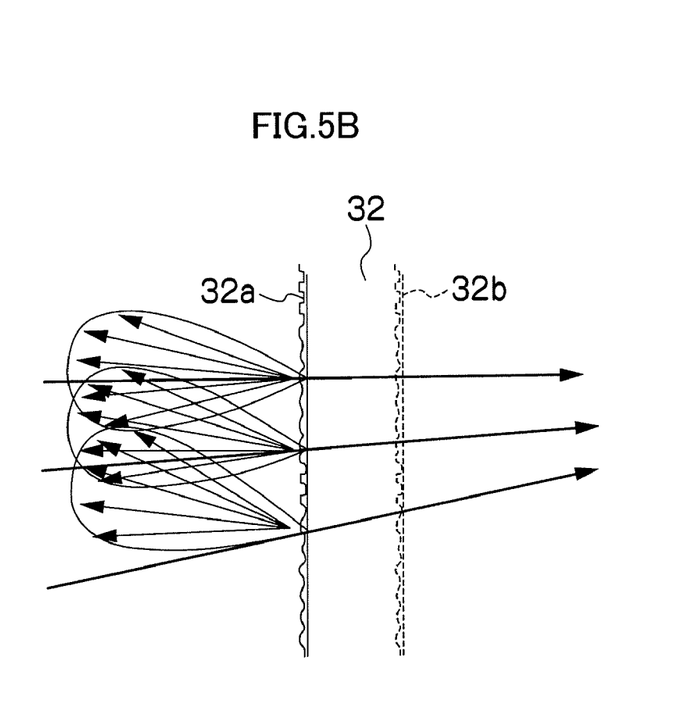

FIGS. 5A and 5B are diagrams showing, as an example, the behavior of a reflected light beam reflected off of the sheath inner surface 32a. FIG. 5A shows a case where a corrugated structure is not formed, while FIG. 5B shows a case where a corrugated structure is formed. When a fine corrugated structure is formed on the sheath inner surface 32a, as shown in FIG. 5B, a portion of the reflected light beam reflected off of the sheath inner surface 32a becomes scattered light beams and scatters across a wide angle as compared to the case where a fine corrugated structure is not formed on the sheath inner surface 32a (FIG. 5A).

Figure 6A:
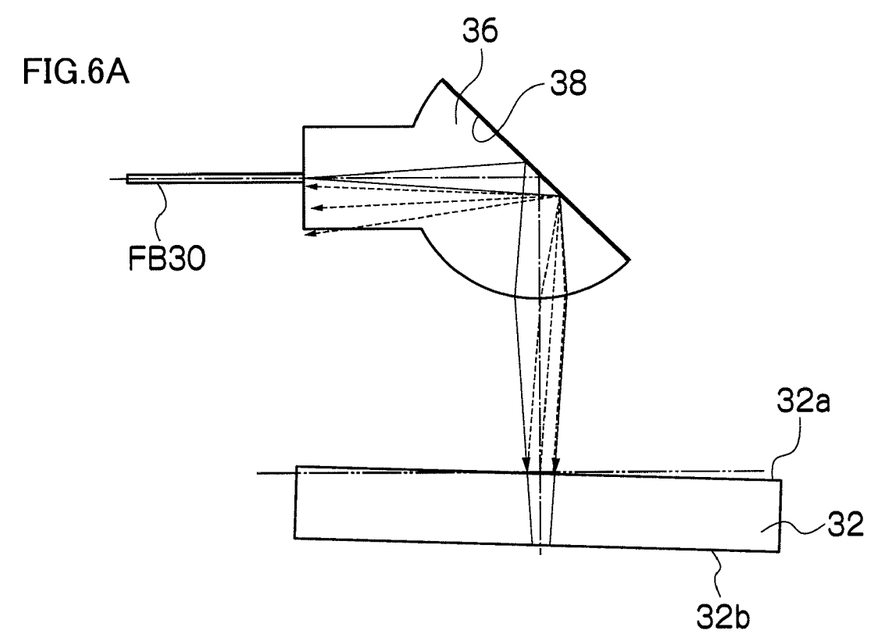
FIGS. 6A and 6B are diagrams showing optical paths of regularly reflected light beams and scattered light beams.
Figure 6B:
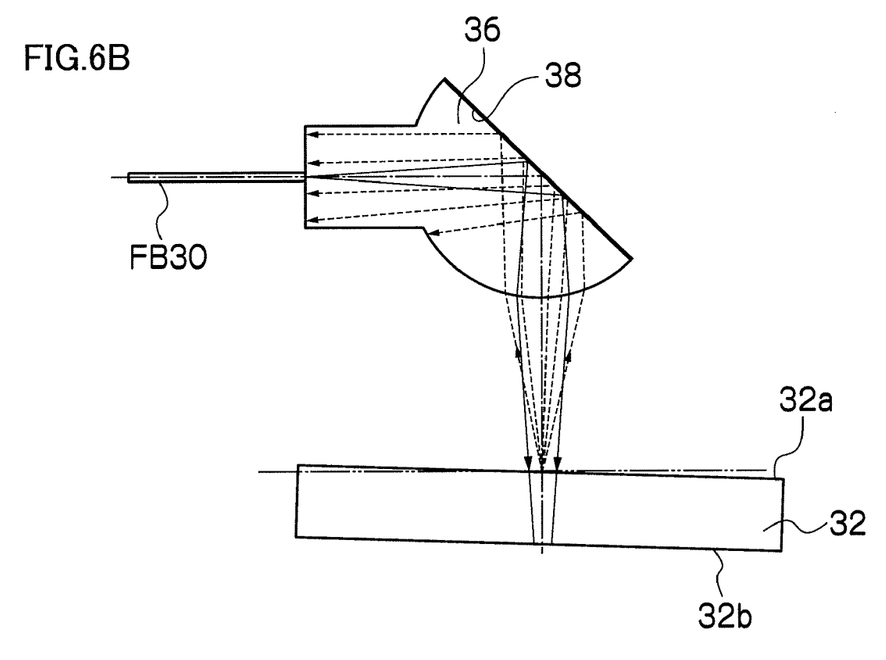

FIGS. 6A and 6B are comparative diagrams of an optical path when the reflected light beam reflected off of the sheath inner surface 32a is a regularly reflected light beam and an optical path when a portion of the reflected light beam reflected off of the sheath inner surface 32a is a scattered light beam. In addition, FIGS. 6A and 6B show a case where the sheath inner surface 32a is oblique to a reference plane. Here, the reference plane is the sheath inner surface 32a when an angle of approximately 90 degrees is formed between the sheath inner surface 32a and the optical axis of the measurement light beam L1 reflected and deflected by the optical lens 36.

A relative angle between the sheath 32 and the optical axis of the measurement light beam L1 varies when the sheath inner surface 32a becomes relatively oblique to the reference plane due to factors such as: a variation in the output angle attributable to the fabrication accuracy of measurement optics such as the optical fiber FB30; the generation of an incline attributable to instability of the sheath inner surface 32a or the sheath outer surface 32b and of measurement optics such as the optical lens 36; and angular variations of the sheath inner surface 32a or the sheath outer surface 32b attributable to bending of the optical probe 30.

In this case, as shown in FIG. 6A, when the reflected light beam reflected off of the sheath inner surface 32a is a regularly reflected light beam, there is a risk that the returning light beam from the sheath inner surface 32a may not enter the optical fiber FB30. Therefore, a rapid light intensity variation of the returning light beam received by the optical fiber FB30 may occur.

However, as shown in FIG. 6B, when at least a portion of the reflected light beam reflected off of the sheath inner surface 32a is a scattered light beam, since the distribution of the returning light beam from the sheath inner surface 32a covers an end face of the optical fiber FB1, the returning light beam from the sheath inner surface 32a reliably enters the optical fiber FB30.

As shown, since the angular dependency of the intensity of a scattered light beam is not as sudden as a regularly reflected light beam, the light intensity of the returning light beam received by the optical fiber FB30 remains stable even when the relative angle between the sheath 32 and the optical axis of the measurement light beam L1 varies.

Accordingly, since the light intensity of the returning light beam received by the optical fiber FB30 is stable, the intensity of a detection signal of the sheath 32 in the OCT signal is prevented from becoming excessively small, thereby enabling the detection signal of the sheath 32 to be reliably detected. In addition, since the intensity of a detection signal of the sheath 32 in the OCT signal does not become excessively large, a detection signal of the measurement object S can be reliably detected.

The corrugated structure is desirably microscopically random since a uniform scattered light distribution can then be realized. In addition, by setting the depths of the asperities to or below ¼ the wavelength $\lambda_{L1}$ of the measurement light beam L1, a phase difference of approximately $\lambda_{L1}/2$ is to be given to the reflected light beam reflected off of the sheath 32 and the amount of the reflected light beam to be scattered can be increased. Meanwhile, a smaller phase difference of approximately $\lambda_{L1}/8$ is to be given to the transmitted light beam at the sheath 32 and the amount of the transmitted light beam to be scattered can be reduced.

Moreover, surface treatment is required to obtain scattered light beams with greater control. When surface treatment cannot be applied over the sheath inner surface 32a or the sheath outer surface 32b of the elongated sheath 32, surface treatment may be separately applied to just the tips thereof, whereby the tips are to be coupled later. The fine asperities may be formed using various techniques such as molding, machine cutting, polishing, and application of fine particles.

Now, if λ denotes the wavelength of an incoming light beam, then an angle $\theta_S$ of a scattered light beam (diffracted light beam) at a position sufficiently distant from a scattering surface with respect to a pitch P of the corrugated structure of the scattering surface can be expressed as follows.

$$\theta_S = \sin^{-1}\frac{\lambda}{P} \qquad \text{[Expression 1]}$$

Here, a "pitch P of the corrugated structure" refers to a distance between adjacent recesses or adjacent protrusions.

For example, for an incoming light beam wavelength λ=1.3 μm, when the angle $\theta_S$ of a scattering light beam is 10 degrees, then the pitch P is around 7.5 μm.

Since the angular distribution of scattered light beams follows the frequency distribution of the corrugated structure, in the present embodiment, in order to obtain scattered light beams that spread across a range of about 10 degrees, for a measurement light beam with a wavelength $\lambda_{L1}$=1.3 μm, forming a random corrugated structure having a minimum period of pitch P=7.5 μm shall suffice. In other words, as the random corrugated structure, forming a structure in which the minimum pitch of asperities is 5 to 6 times the wavelength $\lambda_{L1}$ of the measurement light beam L1 shall suffice.

Moreover, if the wavelength of the measurement light beam L1 is designated by $\lambda_{L1}$, since the 0th dimension does not become zero when the depth of the asperities is less than $\lambda_{L1}/4$, a superposition of a regularly reflected light beam on a scattered light beam occurs.

Therefore, in this case, the incidence angle of the optical axis of the measurement light beam L1 with respect to the sheath 32 is varied until reaching an angle at which the regularly reflected light beam sufficiently attenuates (including variations in the measurement optics). Accordingly, as shown in FIG. 7, the influence of the regularly reflected light beam is eliminated and a rapid variation in the returning light beam due to the angular variation between the sheath surface and the optical axis of the measurement light beam L1 will not occur.

Figure 7:
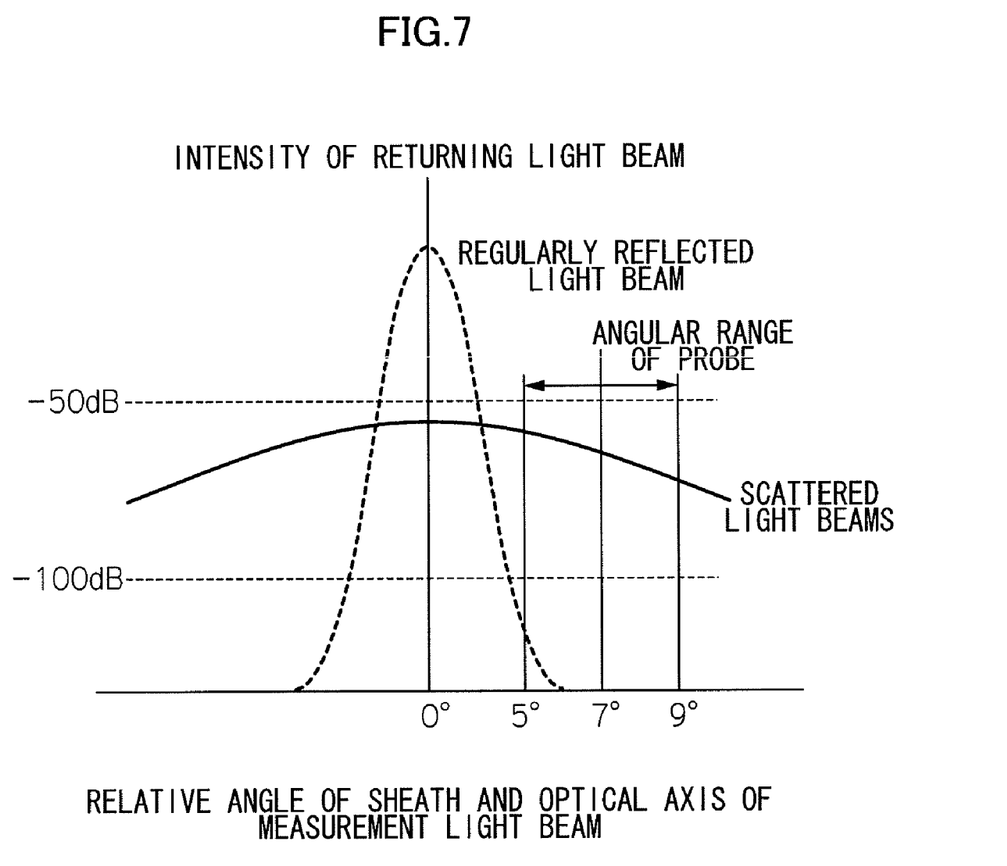
FIG. 7 is a relationship diagram of a relative angle between a sheath and an optical axis of a measurement light beam and a light intensity of a returning light beam.

In FIG. 7, for example, if the variation of the relative angle of the optical axis of the measurement light beam L1 with respect to the sheath inner surface 32a or the sheath outer surface 32b occurring due to the performance of the optical probe 30 is ±2 degrees, by setting the design value of the relative angle of the optical axis of the measurement light beam L1 with respect to the sheath inner surface 32a or the sheath outer surface 32b to 7 degrees, the relative angle of the optical axis of the measurement light beam L1 with respect to the sheath inner surface 32a or the sheath outer surface 32b can be maintained at 5 degrees or more. Consequently, as shown in FIG. 7, the influence of the regularly reflected light beam can be eliminated.

As described above, according to the present invention, since a stable light intensity can be secured for a returning light beam to the optical fiber FB30, a detection signal of the sheath 32 can be reliably detected in an OCT signal and the optical path lengths of the measurement light beam L1 and the reference light beam L2 can be adjusted with precision.

In addition, since a stable light intensity can be secured for a returning light beam to the optical fiber FB30, the value of a detection signal of the sheath 32 can be prevented from becoming excessively large with respect to the value of a detection signal of the measurement object S in an OCT signal and the detection signal of the measurement object S can be reliably detected in an OCT signal.

While an optical tomographic imaging apparatus and an optical probe according to the present invention have been described in detail, it is to be understood that the present invention is not limited to the examples shown above and that various changes and modification can be made without departing from the scope thereof.

What is claimed is:

1. An optical tomographic imaging apparatus comprising:
    an optical path length adjusting device which adjusts an optical path length of a reference light beam split from a source light beam outputted from a light source section;
    an optical probe including an optical fiber to which is entered a measurement light beam split from the source light beam, a lens that deflects and collects the measurement light beam outputted from the optical fiber, and a probe outer casing inside which the optical fiber and the lens are disposed and which is provided with a transmitting surface capable of transmitting the measurement light beam; and
    an interference light detecting device which detects an interference light beam from a multiplexed light beam produced by multiplexing the reference light beam whose optical path length has been adjusted by the optical path length adjusting device with a returning light beam from the optical probe, wherein
    an irregular corrugated structure is formed on the transmitting surface so that a part of a reflected light beam of the measurement light beam reflected off of the transmitting surface becomes scattered light beams.

2. The optical tomographic imaging apparatus according to claim 1, wherein
    the irregular corrugated structure is an irregularly-pitched corrugated structure in which a minimum pitch of asperities of a corrugated structure is several times a wavelength of the measurement light beam.

3. The optical tomographic imaging apparatus according to claim 1, wherein
    a intensity of a reflected light beam of the measurement light beam reflected off of the transmitting surface and received by the optical fiber ranges between −90 dB and −50 dB, inclusive, with respect to a intensity of the measurement light beam outputted from the optical fiber.

4. The optical tomographic imaging apparatus according to claim 2, wherein
    a intensity of a reflected light beam of the measurement light beam reflected off of the transmitting surface and received by the optical fiber ranges between −90 dB and −50 dB, inclusive, with respect to a intensity of the measurement light beam outputted from the optical fiber.

5. The optical tomographic imaging apparatus according to claim 1, wherein
    the irregular corrugated structure is a structure in which a depth of a asperities of a corrugated structure is equivalent to or less than ¼ a wavelength of the measurement light beam.

6. The optical tomographic imaging apparatus according to claim 4, wherein
    the irregular corrugated structure is a structure in which a depth of a asperities of a corrugated structure is equivalent to or less than ¼ a wavelength of the measurement light beam.

7. The optical tomographic imaging apparatus according to claim 1, wherein
    an incidence angle of a optical axis of the measurement light beam with respect to the transmitting surface is an angle such that a light intensity of a regularly reflected light beam is lower than a light intensity of the scattered light beams among the reflected light beam of the measurement light beam reflected off of the transmitting surface and received by the optical fiber.

8. The optical tomographic imaging apparatus according to claim 6, wherein
    an incidence angle of a optical axis of the measurement light beam with respect to the transmitting surface is an angle such that a light intensity of a regularly reflected light beam is lower than a light intensity of the scattered light beams among the reflected light beam of the measurement light beam reflected off of the transmitting surface and received by the optical fiber.

* * * * *